US008817261B2

(12) United States Patent
Borri et al.

(10) Patent No.: US 8,817,261 B2
(45) Date of Patent: Aug. 26, 2014

(54) SURFACE PLASMON FOUR-WAVE MIXING MICROSCOPY

(75) Inventors: Paola Borri, Cardiff South Glamorgan (GB); Wolfgang Langbein, Cardiff South Glamorgan (GB); Francesco Masia, Cardiff South Glamorgan (GB)

(73) Assignee: University College Cardiff Consultants Ltd., Cardiff South Glamorgan (GB)

( * ) Notice: Subject to any disclaimer, the term of this patent is extended or adjusted under 35 U.S.C. 154(b) by 367 days.

(21) Appl. No.: 13/140,163

(22) PCT Filed: Dec. 15, 2009

(86) PCT No.: PCT/GB2009/051718
§ 371 (c)(1),
(2), (4) Date: Sep. 30, 2011

(87) PCT Pub. No.: WO2010/070337
PCT Pub. Date: Jun. 24, 2010

(65) Prior Publication Data
US 2012/0105854 A1    May 3, 2012

(30) Foreign Application Priority Data

Dec. 16, 2008  (GB) .................................. 0822941.1
Aug. 25, 2009  (GB) .................................. 0914847.9

(51) Int. Cl.
*G01N 21/55*    (2014.01)
(52) U.S. Cl.
USPC ........... 356/445; 356/446; 356/318; 356/301; 359/385; 600/318

(58) Field of Classification Search
USPC .......................................... 356/445, 301, 311
See application file for complete search history.

(56) References Cited

U.S. PATENT DOCUMENTS

| | | | |
|---|---|---|---|
| 7,092,086 B2 * | 8/2006 | Knebel | 356/301 |
| 7,480,045 B2 * | 1/2009 | Kung et al. | 356/311 |
| 7,751,053 B2 * | 7/2010 | Carr | 356/445 |
| 2005/0110990 A1 * | 5/2005 | Koo et al. | 356/301 |
| 2005/0164169 A1 | 7/2005 | Malak | |
| 2006/0019313 A1 * | 1/2006 | Andersson et al. | 435/7.1 |
| 2006/0063188 A1 | 3/2006 | Zanni et al. | |
| 2007/0247620 A1 | 10/2007 | Koo | |

FOREIGN PATENT DOCUMENTS

WO    2007011389 A2    1/2007
WO    2007138267 A1    12/2007

OTHER PUBLICATIONS

Masia et al., "Multiphoton microscopy based on four-wave mixing of colloidal quantum dots", Applied Physics Letters 93, 021114 (2008).
Masia F et al., "Resonant four-wave mixing of gold nanoparticles for three-dimensional cell microscopy" Optics Letters, OSA, Optical Society of America, vol. 34, No. 12, Jun. 15, 2009, pp. 1816-1818.

(Continued)

*Primary Examiner* — Tarifur Chowdhury
*Assistant Examiner* — Isiaka Akanbi
(74) *Attorney, Agent, or Firm* — Fitch, Even, Tabin & Flannery, LLP

(57) ABSTRACT

Laser pulses are applied to surface plasmon resonant articles such as gold nanoparticles within a microscopy sample to generate a four-wave mixing signal that is detected as the output of the microscopy process.

20 Claims, 4 Drawing Sheets

(56) References Cited

OTHER PUBLICATIONS

Hashimoto M, "Coherent anti-strokes raman microscope for identification of cellular molecule", IEEE—The Second Asian and Pacific Rim Symposium on Biophotonics; Dec. 14, 2004, pp. 234-235.

Ichimura et al., "Local enhancement of coherent anti-Stokes Raman scattering by isolated gold nanoparticles", Journal of Raman Spectroscopy Wiley UK LKND, vol. 34, No. 9, Sep. 2003, pp. 651-654.

Hayazawa Norihiko et al., "Amplification of coherent anti-Stokes Raman scattering by a metallic nanostructure for a high resolution vibration microscopy", Journal of Applied Physics, American Institute of Physics, New York, vol. 95, No. 5, Mar. 1, 2004, pp. 2676-2681.

Masselin P. et al., "Surface Plasmon enhanced SFG and FWM of femtosecond pulses of non-sinusoidal metal grating", Technical Digest, Summaries of Papers Presented at the Quantum Electronics and Laser Science Conference, vol. 1, 2002, pp. 257-258.

Kawata S, et al., "Tip-enhanced near-field CARS microscopy for molecular nano-imaging", Proceedings of the SPIE—The International Society for Optical Engineering SPIE-INT. Soc. Opt. Eng USA LNKD—D0I:10.1117/12.596664, vol. 5700, No. 1, 2005, pp. 52-59.

Kawata S. et al., "Coherent anti-Stokes Raman spectroscopy for nano-imaging with a metallic near-field probe", Proceedings of SPIE—The International Society for Optical Engineering—Nonlinear Optical Transmission and Multiphoton Processes in Organics II 2004 SPIE US LNKD—D0I10:1117/12.564283, vol. 5516, 2004, pp. 1-8.

Liang E. J. et al., "Experimental observation of surface-enhanced coherent anti-Stokes Raman scattering", Chemical Physics Letters, North-Holland, Amsterdam LNKD—D0I:10.1016/0009-2614(94)00779-9, vol. 227, No. 1-2, Sep. 2, 1994, pp. 115-120.

Danckwerts M. et al., "Optical frequency mixing at coupled gold nanoparticles", Physical Review Letters 2007 American Physical Society US LNKD—D0I:01.1103/PHYSREVLETT.98.026104, vol. 98, No. 2, 2007.

Tamil Selvan S. et al., "Sol-gel derived gold nanoclusters in silica glass processing large optical nonlinearities", Journal of Physical Chemistry B ACS USA LNKD—D0I:10.1021/JP020860X, vol. 106, No. 39, Oct. 3, 2002, pp. 10157-10162.

International Search Report for PCT/GB2009/051718 dated May 12, 2012.

* cited by examiner

SURFACE PLASMON FOUR-WAVE MIXING MICROSCOPY

CROSS REFERENCE TO RELATED APPLICATIONS

This application is a national phase application of International Application No. PCT/GB2009/051718, filed Dec. 15, 2009, claiming priority to Great Britain Applications No. 0822941.1, filed Dec. 16, 2008, and No. 0914847.9, filed Aug. 25, 2009, both of which are incorporated by reference herein in their entirety.

FIELD

The invention relates to the field of investigating sample material by probing it with electromagnetic radiation and examining the resulting stimulated electromagnetic emissions.

BACKGROUND

Optical microscopy is presently the pre-eminent technique for the investigation living cells and tissues. It is known to label biological cells with markers that are stimulated to emit electromagnetic radiation when interrogated with a particular kind of electromagnetic radiation. For example, the markers could be made of fluorescent material or they could be semiconductor nanocrystal quantum dots. In the latter case, see "Multiphoton microscopy based on four-wave mixing of colloidal quantum dots", Masia et al, Applied Physics Letters 93, 021114 (2008).

SUMMARY

The invention is defined in the appended claims, to which reference should now be made.

BRIEF DESCRIPTION OF THE DRAWINGS

By way of example only, certain embodiments of the invention will now be described with reference to the accompanying drawings, in which.

DETAILED DESCRIPTION

Figure 1:
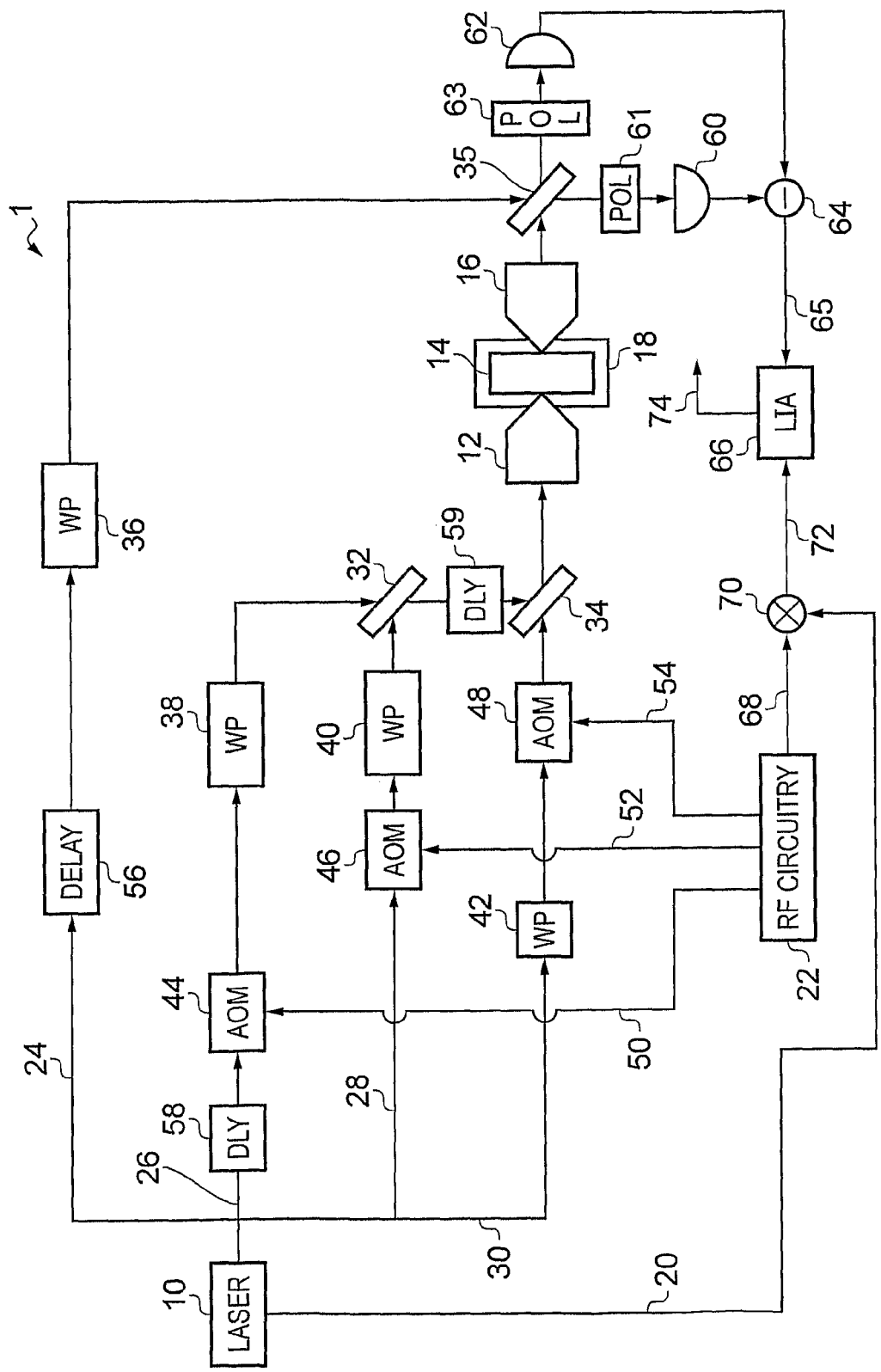
FIG. 1 is a block diagram schematically illustrating an optical microscope setup for four-wave mixing microscopy.

FIG. 1 shows an optical microscope 1 that is driven by a laser 10. An objective lens 12 focuses light from the laser 10 into a focal volume within a sample 14 and another objective lens 16 captures light that is emitted from that focal volume. The sample 14 is mounted on a stage 18 that has a piezoelectric drive for moving the sample in one or more of three mutually orthogonal directions in order to scan the aforementioned focal volume through the sample 14.

The laser 10 is self mode-locked and emits pulses of 150 fs duration at a repetition rate of 76 MHz. The pulses emitted by the laser have a centre frequency in the range between 530 nm and 550 nm and a spectral width of approximately 4 nm. This centre frequency is matched to the surface plasmon resonance frequency of gold nanoparticles (GNPs) that will be used in conjunction with the microscope 1. The train of pulses emitted by the laser 10 is conveyed in parallel along four optical paths 24, 26, 28 and 30. Path 24 is a reference path whose pulses are combined with the light that is picked up from the sample 14 by objective lens 16, whereas paths 26, 28 and 30 are interrogation paths that deliver light to the sample 14 through objective lens 12. The light from interrogation paths 26 and 28 is combined at 50:50 beam splitter 32. The light emerging from the beam splitter 32 is then combined with the light from interrogation path 30 at 50:50 beam splitter 34. The light emerging from beam splitter 34 is then applied to the objective lens 12. The light travelling along the reference path 24 is combined with the light collected by the objective lens 16 at a 50:50 beam splitter 35.

The four paths 24 to 30 each contain a respective wave-plate (phase retarder) 36 to 42. The wave-plates 38 and 40 are adjusted to impose parallel linear polarisations on the laser pulse trains from paths 26 and 28 at the position of the focal volume. The wave-plates 36 and 42 are arranged to impose parallel linear electric field polarisations upon the laser pulse trains travelling along paths 24 and 30. The linear electric field polarisation imposed by wave-plates 36 and 42 is orthogonal to the linear electric field polarisation that is imposed by wave-plates 38 and 40.

Each of paths 26 to 30 contains a respective acousto-optic modulator 44, 46, and 48. Acousto-optic modulator 44 receives at a control input an RF signal 50 of frequency $v_1$ that has been generated by the RF circuitry 22. The acousto-optic modulator 44 functions so as to shift the laser pulses up in frequency by an amount equal to $v_1$. Similarly, a control input of acousto-optic modulator 46 is supplied with an RF signal 52 of frequency $v_2$ so as to cause the laser pulses passing through that modulator to be shifted up in frequency by an amount equal to $v_2$. Likewise, a control input of acousto-optic modulator 48 is fed with an RF signal 54 of frequency $v_3$ such that the laser pulses passing through that modulator are upshifted in frequency by an amount equal to $v_3$. In one example, $v_1=80$ MHz, $v_2=81.6$ MHz and $v_3=79$ MHz.

Paths 24 and 26 include respective delay elements 56 and 58, and a further delay element 59 is also placed between beam splitters 32 and 34. The delays 56, 58 and 59 can take the form of glass blocks or path length extensions specified by adjustable mirror arrangements. Consider a given pulse emitted by the laser 10. To a reasonable approximation, the delay element 58 is designed so that the versions of this pulse conveyed by paths 26 and 28 will arrive simultaneously at beam splitter 35. As for the versions of that pulse that are conveyed along paths 24 and 30, the delay elements 56 and 59 are designed such that these two versions of the pulse arrive simultaneously at the beam splitter 35 but at a time delay $\tau$ after the two versions of the pulse delivered by paths 26 and 28.

Light from the beam splitter 35 arrives at a pair of balanced photo diodes 60 and 62 via respective polarizers 61 and 63. Polarizers 61 and 63 are polarised in parallel with the light polarisation in path 24 and 30 but orthogonal the light polarisation in path 26 and 28 such that light that has the polarisation of paths 26 and 28 is excluded from the photo diodes 60 and 62 but light having the polarisation of paths 24 and 30 is admitted to the photo diodes. A signal 65 representing the difference in the output signals of the photo diode 60 and 62 is formed by a subtractor 64. The difference signal 65 is delivered to a lock-in amplifier 66. The RF circuitry 22 is arranged to generate a signal 68 of frequency $v_2-v_1+v_3$. Arrangements of mixer circuits that can use the RF signals 50, 52 and 54 to generate signal 68 will be known to persons skilled in the art of RF engineering. The laser 10 contains a photodiode within its lasing cavity and the output of this photodiode is an electrical signal 20 at the pulse repetition rate (76 MHz) of the laser. The signal 68 is then mixed in a mixer 70 with the signal 20. The signal 72 that results from this mixing process is applied to an input of the lock-in amplifier 66. The lock-in amplifier 66 functions to produce an output signal 74 that is in effect an amplification of that part of the spectrum of signal 65 that matches the frequency content of signal 72. The signal 74 is supplied to other electronics to enable 2D and 3D images of the sample 14 to be assembled. Having described the nature of the optical arrangement and electronic circuits of the microscope 1, we will now go on to describe the physics of the present microscopy technique.

The sample 14 contains biological cells that have been stained with GNPs. Techniques for achieving this will be apparent to persons skilled in the art of cell microscopy. Energy from the pulses of the laser 10 is absorbed by surface plasmons in the GNPs and some of this energy is re-radiated as light that is picked up by the objective lens 16. We will now consider the effect of a single pulse from laser 10 upon a single GNP within the part of the sample 14 that lies in the focal volume.

Figure 2:
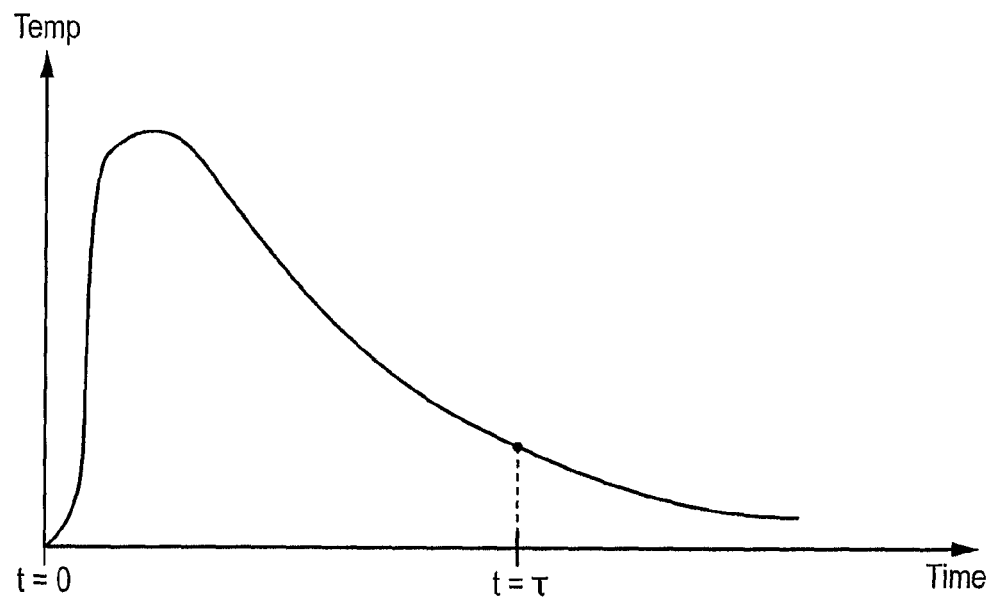
FIG. 2 is a plot illustrating temporal variation of the free electron temperature in metallic nanoparticles after optical excitation.
Figure 3:
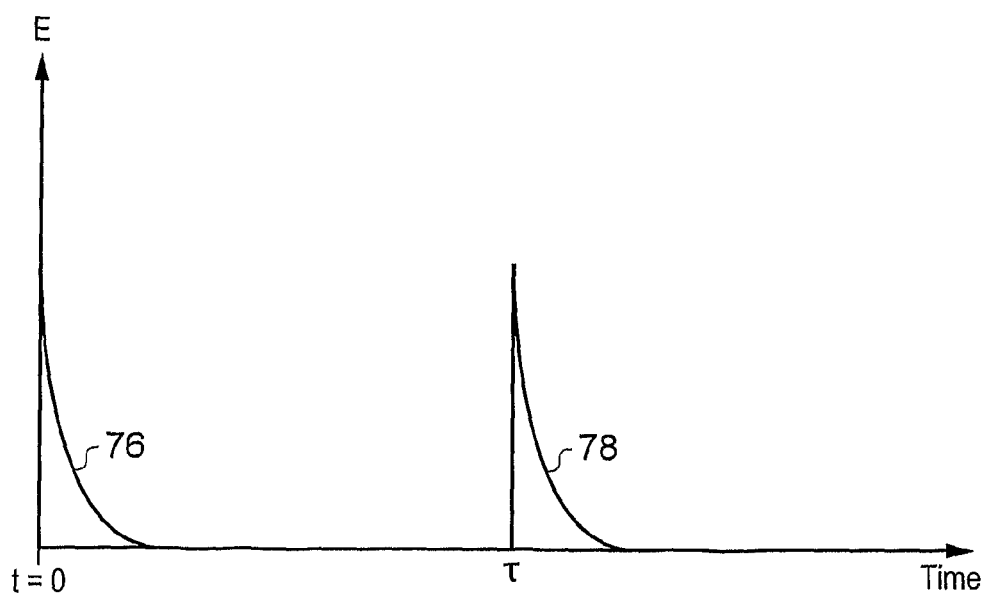
FIG. 3 is a plot illustrating light re-radiated from markers within a sample positioned within the microscope.

Two versions of this pulse arrive simultaneously at the sample 14 via paths 26 and 28 and excite a surface plasmon in the GNP. The surface plasmon can be thought of as a collective oscillation of the free electrons within the GNP. The energy of this collective excitation is converted within its lifetime into a temperature increase of the free electrons, hereinafter called the "free electron temperature". FIG. 2 is a plot illustrating how the free electron temperature of the GNP changes after application of a delta-like laser pulse and FIG. 3 is a plot of the electric field amplitude of the light emitted by the GNP in response to the three versions of a delta-like laser pulse that arrive along paths 26, 28 and 30. The surface plasmon lifetime can be considered as the rise time of the curve in FIG. 2 or the decay time of pulse 76 or 78 in FIG. 3. In the realisation of FIG. 1 the pulses emitted by the laser 10 have a time duration larger that the surface plasmon lifetime but shorter than the delay $\tau$.

In FIG. 2 then, the two versions of the pulse that are delivered via path 26 and 28 arrive at the GNP simultaneously at time t=0. As can be seen in FIG. 2 the application of this radiation causes a rapid increase in the free electron temperature, which reaches a peak and then decays in an exponential fashion. The time $\tau$ at which the version of the pulse from path 30 arrives at the GNP is also shown in FIG. 2. It will be apparent that at time $\tau$, the free electron temperature is still elevated significantly relative to time t=0.

After the application of the versions of the pulse that travel along paths 26 and 28, some of the energy that was absorbed from the laser radiation is re-radiated as light, which exponentially decays in a rapid fashion. This pulse of re-radiated light is indicated 76 in FIG. 3. In a similar manner, another exponentially decaying pulse of re-radiated light commences at time t=$\tau$ in response to the version of the pulse that is delivered via path 30. This second pulse of re-radiated light is indicated 78 in FIG. 3. It is to be noted that, in order to achieve clarity of illustration, the exponential decay rates of pulses 76 and 78 have been shown as much less severe than they actually are in practice.

The nature of the pulse 78 that is emitted at time t=$\tau$ is to a certain extent determined by the laser radiation that was applied to the GNP at time t=0. This is because the nature of the surface plasmon resonance frequency of the GNP will depend upon the free electron temperature of the GNP, and the free electron temperature at time t=$\tau$ is elevated by reason of application of laser radiation at time t=0.

Figure 4:
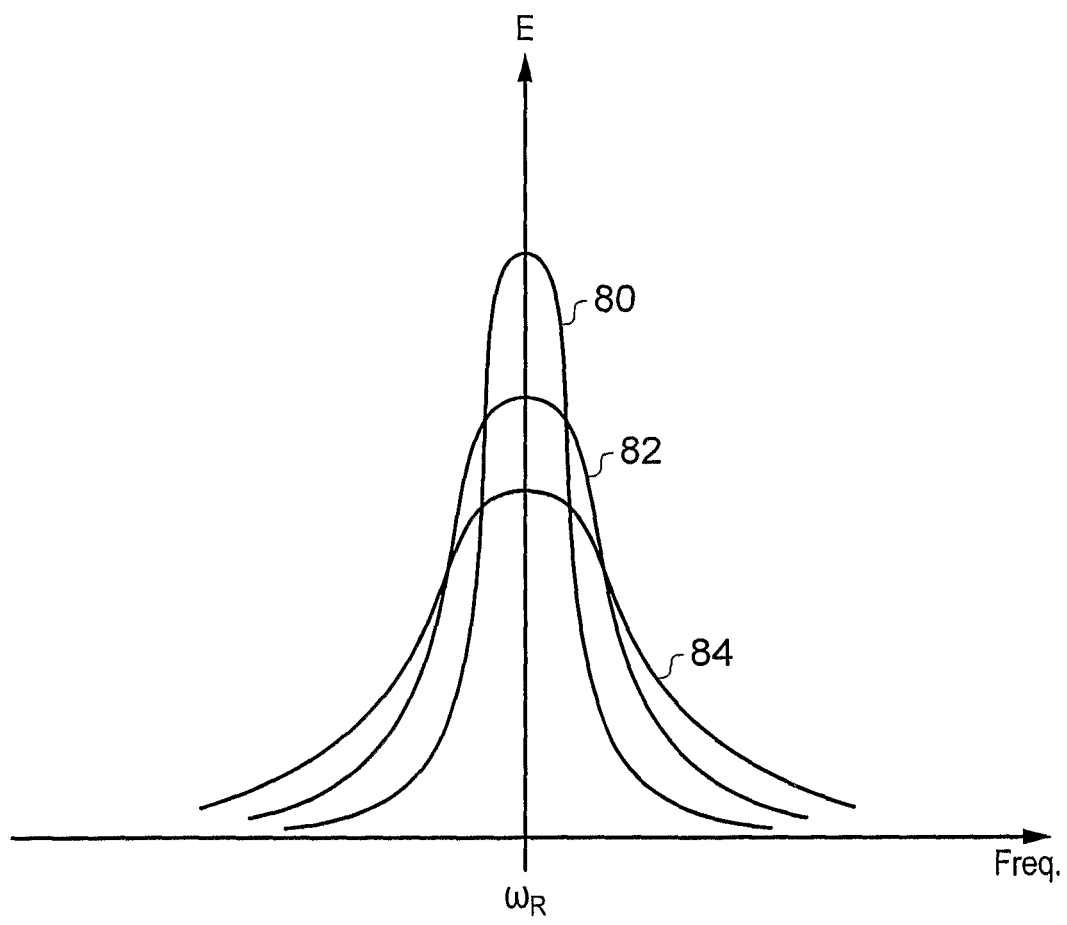
FIG. 4 is a plot illustrating variation in surface plasmon resonance with electron temperature.

FIG. 4 illustrates how the surface plasmon resonance changes with free electron temperature and shows the surface plasmon resonance for three different free electron temperatures. Although the centre frequency of the surface plasmon resonance will be different for each of these temperatures, these centre frequencies are shown overlying one another in FIG. 4 to facilitate an appreciation of how both the height of the peak and its full width at half maximum vary with changes in the free electron temperature. Essentially, the higher the temperature, the lower and wider the resonance peak becomes. Thus, traces 80, 82 and 84 relate to successively higher free electron temperatures.

The change of pulse 78 by the heating is in fact a product of three interacting versions of the applied laser pulse. Pulse 78 is triggered at t=$\tau$ by the version of the pulse that travels along path 30 but the nature of pulse 78 is in part determined by the two versions of the pulse that arrive at the GNP at time t=0 via paths 26 and 28. Therefore, the three versions of the given laser pulse interact with the GNP in a coupled fashion, in a phenomenon known as four-wave mixing. It will be recalled that the three versions of the train of laser pulses that are sent along paths 26, 28 and 30 are altered slightly in frequency by their respective acousto-optic modulators 44, 46 and 48. The four-wave mixing that occurs at the GNP leads to a component in pulse 78 that is higher in frequency than the centre frequency of the laser pulses by an amount $v_2-v_1+v_3$, this amount being 80.6 MHz in the case of the example frequency set given earlier. This component arises from the mixing of the three versions of the applied laser pulse. Henceforth, this component of pulse 78 shall be referred to as the "FWM signal".

The FWM signal from the GNP is collected by the objective lens 16 and is conveyed to the beam splitter 35. The version of the laser pulse that is conveyed through the reference path 24 arrives at the beam splitter 35 at the same time as the FWM signal. The FWM signal has a polarisation that is dictated by the wave-plate 42 because the FWM signal is essentially a re-radiation of the version of the pulse that travels along path 30. Accordingly, the versions of the FWM signal that emerge from the beam splitter 35 have polarisations that are aligned with those of polarisers 61 and 63 with the result that the two versions of the FWM signal are admitted to respective ones of the photo diodes 60 and 62. Since polarisers 61 and 63 are aligned with the polarisation dictated by the wave-plate 36, the beam splitter 35 also delivers to photo diodes 60 and 62 respective versions of the version of the laser pulse that arrives via the reference path 24. However, signal energy from the versions of the pulses conveyed by paths 26 and 28 cannot reach the photo diodes 60 and 62 because the polarisation of polarisers 61 and 63 is orthogonal to that of dictated by the wave-plates 38 and 40. The polarisers 61 and 63 also prevent energy from pulse 76 from reaching the photo diodes 60 and 62. This is because pulse 76 has the same polarisation as that dictated by the wave-plates 38 and 40 (which deliver the energy that is re-radiated to create pulse 76) and this polarisation is orthogonal to polarisers 61 and 63.

At each of the photo diodes 60 and 62, the arriving part of the FWM signal and the arriving part of the version of the pulse from the reference path 24 interfere with one another because they emanate, ultimately from the same pulse of light from a coherent source, namely laser 10. This interference effectively causes photo diodes 60 and 62 to each output an electrical signal whose frequency is equal to the result of downconverting the FWM signal by an amount equal to the centre frequency of the laser pulses. That is to say, each of the photo diodes 60 and 62 produces, in response to the arriving light, an electrical signal at an RF frequency equal to $v_2-v_1+v_3$. Due to the interference occurring in the light reaching the photo diodes 60 and 62, each of the photo diodes will experience a time varying illumination intensity. Due to the principle of conservation of energy, if the illumination intensity experienced by photodiode 60 decreases, then the illumination intensity experienced by photodiode 62 will correspondingly increase. Subtractor 64 produces a signal 65 which represents the difference in the outputs of 60 and 62. Thus, a signal representative of the downconverted FWM signal is recovered, whilst background elements in the electrical outputs of the photo diodes 60 and 62 are rejected by the subtraction process. This is a type of common mode rejection scheme.

Up to this point, we have been considering the effect on a single GNP of an exemplary pulse of the train emitted by the laser 10. For present purposes, it can be assumed that all of the GNPs in the focal volume that is specified by the objective lenses 12 and 16 respond in the same way, meaning that the magnitude of the difference signal 65 is proportional to the number of GNPs that are presently located within the focal volume. If one takes into consideration that the laser is emitting pulses at a repetition rate of 76 MHz, then, on a wider timescale, the signal 65 can be regarded as being a continuous signal of frequency $v_2-v_1+v_3$ that has been downconverted in frequency by a signal having the frequency of the pulse repetition rate of the laser.

As was discussed earlier, the RF circuitry 22 is arranged to produce a signal 68 of frequency $v_2-v_1+v_3$. Signal 68 is then mixed in mixer 70 with signal 20, whose frequency is the pulse repetition rate of the laser 10, in order to produce a downconverted reference signal 72 for the lock-in amplifier 66. (In the case of the exemplary frequency set given earlier, the reference signal 72 would have a frequency of 80.6 MHz-76 MHz=4.6 MHz.) That part of signal 65 that has the same frequency content as signal 72 is then amplified by the lock-in amplifier 66 to produce an output signal 74. Therefore, it can be seen that output signal 74 is an amplification of that part of signal 65 that is the FWM signal.

The signal 74 is an imaging result for the part of the sample 14 that falls within the focal volume of the objective lenses 12 and 16. Different parts of the sample 14 can be measured by moving the sample 14 using the piezo-electric stage 18. Thus, it is possible to take values of the output signal 74 for different volumes within the sample 14 and thus build up a three dimensional image of the sample. Two principle advantages of the microscope 1 over known techniques will now be discussed.

The microscope 1 images GNP labels via a four-wave mixing process mediated by surface plasmons of the GNPs. The intensity of the FWM signal reaching the photo diodes is several orders of magnitude greater than the corresponding signal in the FWM microscopy technique in the aforementioned paper by Masia et al that is mediated by light absorption by, and re-radiation from, semiconductor CdSe quantum dots. In the system described in that paper, a sample is probed by delivery of just two simultaneous versions of a laser pulse to bring about a four-wave mixing signal. However, that four-wave mixing signal is masked to a certain extent by other radiation stimulated by the applied pulse pair and able to interfere with the pulse from the reference path 24 (e.g., instantaneous optical nonlinearities of water molecules within the sample). In contrast, with microscope 1, the FWM signal is produced by a pulse through path 30 which is delayed by an amount τ such that the FWM signal is triggered at a time after effects such as instantaneous optical nonlinearities upon application of the initial pulse pair (from paths 26 and 28) has subsided. Accordingly the FWM signal produced by microscope 1 has an appreciably better signal to noise and signal to background ratio as compared with the earlier Masia et al arrangement.

It will be apparent to the skilled person that various details of the described embodiment can be varied.

For example, wave-plates 38 and 40 could be replaced by a single wave-plate located between beam splitters 32 and 34.

Also, it was assumed so far that the GNPs are homogenous. Instead, different types of GNPs could be used together, each type having a unique combination of size and shape and therefore a different surface plasmon resonance frequency. These different types of GNPs could be used to label different features within the sample 14, with the result that the centre frequency of the pulses of the laser 10 could be tuned to allow the imaging of first one particular type of GNP marker, and then GNP markers of another type, and so on.

The nanoparticles need not be made of gold but can made of any substance that can support surface plasmons, and which, preferably, is biologically inert. For example, platinum nanoparticles could be used.

The free electron temperature in FIG. 2 exhibits a decrease after the initial peak. This decrease is caused by kinetic energy transferring over time from the free electrons of the GNP to the lattice of gold atoms within the nanoparticle. Thus, the vibrational energy of the gold lattice increases and therefore the temperature of the GNP itself increases. This mechanism for heating the GNPs can be exploited in as much as the power of the laser pulses can be increased up to a point where the GNPs become heated sufficiently to disassociate themselves from the sample features to which they are attached. Thus, a mechanism for removing markers from a sample is also provided.

When two nanoparticles touch or come close together, say exhibiting a separation of less than about 1 nm, then they can form a dimer. Whereas the nanoparticles individually have a surface plasmon resonance at about 530 nm, when two such particles form a dimer the resonances shifts significantly towards 700 nm. In one variant then, the laser could be tuned to the dimer resonance frequency so that dimers, rather than individual GNPs are imaged. This can be useful in the context of, for example, imaging interactions of biological elements carrying the GNPs.

The embodiments described above use light to image GNPs. Such particles are also used as markers in electron microscopy. Therefore, it is possible to make comparisons between an image captured using one of the embodiments described above and an image of the same sample as captured by an electron microscope. Moreover, an image captured using one of the embodiments described above could be used to guide the capture of an electron microscope image. That is to say, an area of a sample that is to be subjected to electron microscopy could be selected on the basis of an image of a wider area of the sample as captured using one of the embodiments described above. This provides an advantage in that resources need not be wasted by applying an electron microscope to uninteresting areas of the sample.

In another embodiment, CdSe quantum dots are used as markers instead of GNPs. In that case, the laser is tuned appropriately so that its pulses match the frequency of the resonance due to the semiconducting properties of the dots.

In the embodiments described thus far, pulses through paths 26 and 28 arrive at the focal volume simultaneously. It is possible however to adjust delay 58 so that pulses from path 26 arrive later than their counterparts from path 28. However, this delay needs to be less than the dephasing time of the markers in order that signal 65 will be appreciable. If this delay is just sufficient to cause each pulse from path 26 to arrive just as its counterpart from path 28 has ceased and the pulse duration is shorter than the dephasing time, then the signal 65 will be boosted. In the case where the four-wave mixing light is mediated by the surface plasmon effect, however, the dephasing time is so short (much shorter than the pulse duration) that in practice the pulses from paths 26 and 28 are delivered simultaneously.

Figure 5:
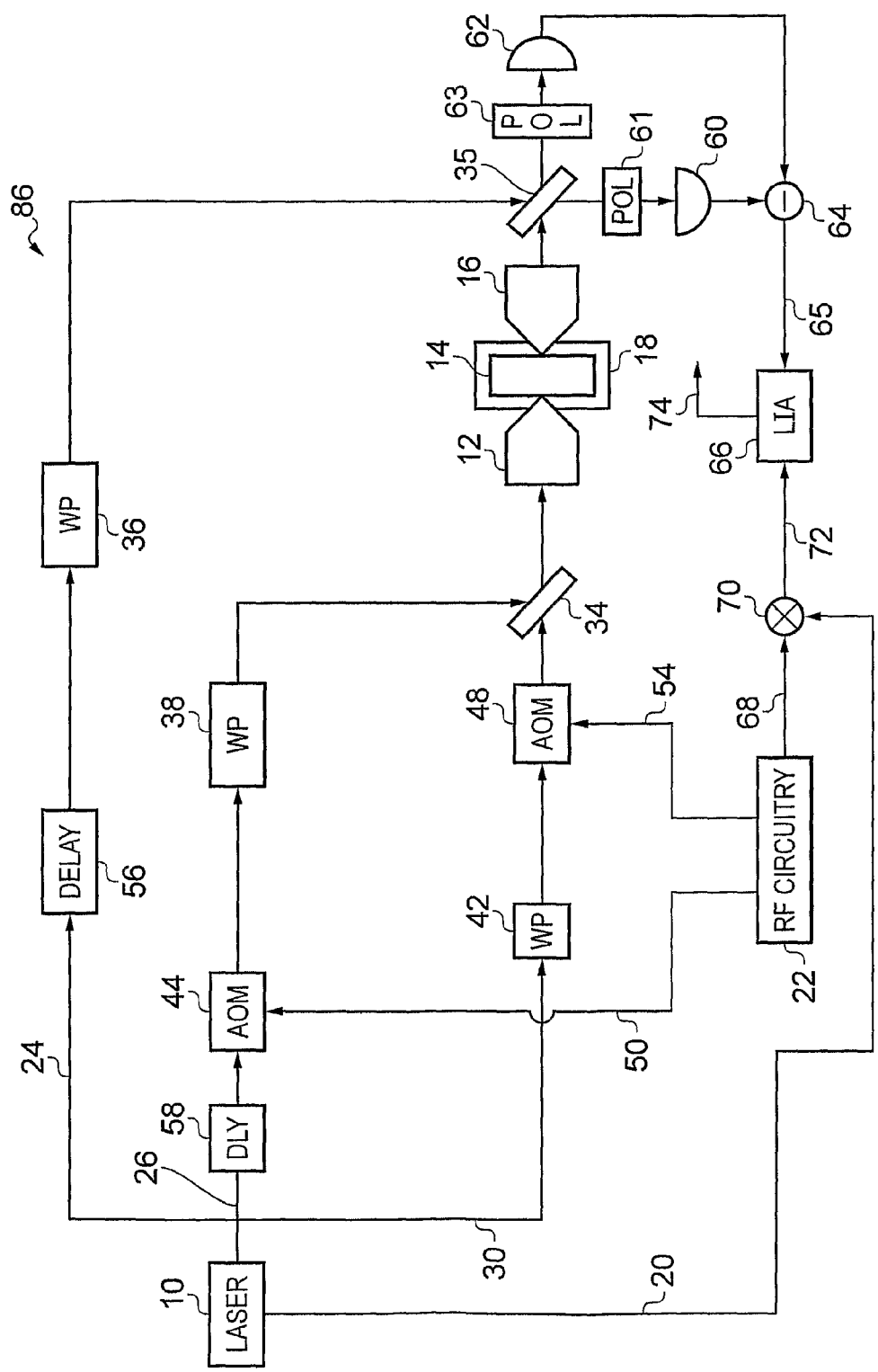
FIG. 5 is a block diagram schematically illustrating a variant of the microscope of FIG. 1.

In FIG. 5, a further variant, 86, of the microscope 1 is illustrated. In FIG. 5, elements that have been carried over from FIG. 1 retain the same reference numerals. Microscope 86 differs from microscope 1 primarily through the omission of path 28, the associated acousto-optic modulator 46, the associated wave-plate 40, the beam splitter 32 and the delay element 59. Thus, the construction of microscope 86 is simpler than that of microscope 1.

The purpose of path 28 in microscope 1 is to generate a pulse than can combine at the sample 14 with a pulse from path 26 to excite a surface plasmon in a GNP. In microscope 86, the RF circuitry 22 is adapted to compensate for the removal of path 28, as will now be explained.

The RF circuitry 22 is adapted to send a signal over line 50 that causes acousto-optic modulator 44 to convert a pulse from laser 10 into two pulses that have been shifted up in frequency by amounts that differ by a frequency of $v_2-v_1$. These two pulses can interact at a GNP in the sample 14 to excite a surface plasmon which can in turn interact with a pulse from path 30 (in the manner described with reference to FIGS. 2 to 4) to create a pulse like pulse 78 containing a "FWM signal" that is higher in frequency than the centre frequency of the pulses emitted by the laser 10 by an amount $v_2-v_1+v_3$, which is the same result as in microscope 1.

In order to create the two differently shifted versions of a laser pulse in path 26, the RF circuitry 22 drives the acousto-optic modulator 44 with a signal that is in effect a superposition of two signals whose frequencies are $v_1$ and $v_2$ respectively. To achieve this, the signal delivered over line 50 can be a signal of frequency $$\frac{1}{2}(v_2 + v_1)$$

whose intensity is modulated with a signal of frequency $(v_2-v_1)$.

In microscope 1, the delay element 58 functions to control the time of arrival at the focal volume of a pulse from path 26 relative to the time of arrival at the focal volume of the corresponding pulse from path 28. In microscope 86 however, the delay element 58 serves to control the parameter τ (FIGS. 2 and 3). The ability to control the delay between pulses that interact to excite a surface plasmon (as conferred by delay element 58 in microscope 1) is useful when the markers that are being imaged have a dephasing time that is longer than the duration of the laser pulses. However, where the markers are GNPs, the dephasing time is shorter than the laser pulse duration.

In the embodiments described thus far, transmission microscopy has been used, with the sample 14 located between the objective lenses 12 and 16. It is possible to adopt instead an epi-geometry where a single objective lens is used to deliver light to and collect light from the sample. As will be appreciated by persons skilled in the art of microscope design, a beam splitting scheme would need to be used in conjunction with the single objective lens to couple light from the laser 10 into the sample 14 and to direct light from the sample 14 into the detection scheme based on the photo diodes 60 and 62. An advantage of an epi-geometry approach is that it uses only a single objective, which is more compatible to commercial microscope designs. Furthermore when using epi-geometry the laser beam onto the single objective lens can be made steerable to scan the focal volume over the sample, rather than using translatable stage 18, such that when the beam is steering the interference of the reference beam 24 and of the epi-detected light from the sample is maintained (de-scanned geometry).

The invention claimed is:

1. A microscope comprising:
   an illumination source arranged to illuminate a sample zone with stimulation light that is absorbed by a marker, if present in the sample zone, and is emitted as four-wave mixing light, and
   a detector arranged to discriminate the four-wave mixing light in light emanating from the sample zone,
   wherein the illumination source comprises:
      a light source that emits a train of pulses of laser light, and
      an arrangement of parallel optical paths configured to received said train of pulses, and
   wherein said arrangement of parallel optical paths is configured to:
      create first, second and third versions of a single pulse of said train of pulses, and
      deliver said first, second and third versions of said single pulse to the sample zone such that the third version arrives at the sample zone after the second version and the second version arrives at the sample zone not earlier than the first version and not later than the first version by more than the dephasing time of the marker, and
   wherein the detector is configured to bring a fourth version of the said single pulse into interaction with the light emanating from the sample zone and the detector is configured to detect interference of the fourth version of said single pulse with four-wave mixing light triggered by the third version of said single pulse.

2. The microscope according to claim 1, wherein the illumination source is arranged to deliver said first and second versions of said single pulse to the sample zone at the same time.

3. The microscope according to claim 1, further comprising a frequency modulator arranged to cause the first, second and third versions of said single pulse to be displaced in frequency relative to one another.

4. The microscope according to claim 3, wherein the frequency modulator is arranged to use acousto-optic modulation to displace the first, second and third versions of said single pulse relative to one another in terms of frequency.

5. The microscope according to claim 1, wherein said arrangement of parallel optical paths comprises first and second delivery paths, the first path is arranged to deliver the first and second versions of said single pulse to the sample zone and the second path is arranged to deliver the third version to the sample zone.

6. The microscope according to claim 5, wherein at least the first path comprises a respective acousto-optic modulator.

7. The microscope according to claim 6, further comprising a signal generator for driving the acousto-optic modulator in the first path with a signal that modifies said single pulse into said first and second versions.

8. The microscope according to claim 1, wherein said arrangement of parallel optical paths comprises first, second and third delivery paths, the first path is arranged to deliver the first version of said single pulse to the sample zone, the second path is arranged to deliver the second version to the sample zone and the third path is arranged to deliver the third version to the sample zone.

9. The microscope according to claim 8, wherein at least two of the first, second and third paths comprise a respective acousto-optic modulator.

10. The microscope according to claim 1, wherein the marker is a surface plasmon resonant gold particle.

11. The microscope according to claim 1, wherein the marker is a dimer.

12. The microscope according to claim 1, wherein said light source is a laser.

13. A method of performing microscopy on sample material, the method comprising:
    illuminating the sample material with stimulation light that will be absorbed by a marker and will be emitted as four-wave mixing light; and
    discriminating the four-wave mixing light in light emanating from the sample zone;
    wherein illuminating the sample material comprises:
        emitting a train of pulses of laser light, and
        receiving said train of pulses in an arrangement of parallel optical paths, and
    wherein said arrangement of parallel optical paths is configured to:
        create first, second and third versions of a single pulse of said train of pulses, and
        convey first, second and third versions of said single pulse of laser light to the sample zone such that the third version arrives at the sample zone after the second version and the second version arrives at the sample zone not earlier than the first version and not later than the first version by more than the dephasing time of the marker,
    wherein the method further comprises:
    bringing a fourth version of said single pulse into interaction with the light emanating from the sample zone, and
    wherein discriminating the four-wave mixing light comprises:
    detecting interference of the fourth version of said single pulse with four-wave mixing light triggered by the third version of said single pulse.

14. The method according to claim 13, further comprising applying the stimulation light again at higher power such that sufficient energy is absorbed into a surface plasmon of the marker to disassociate the marker from the sample material.

15. The method according to claim 13, wherein said arrangement of parallel optical paths is configured to convey said first and second versions of said single pulse to the sample zone at the same time.

16. The method according to claim 13, further comprising adjusting the first, second and third versions of said single pulse to be displaced in frequency relative to one another.

17. The method according to claim 13, wherein said light source is a laser.

18. The method according to claim 13, wherein the marker is a surface plasmon resonant gold particle.

19. The method according to claim 13, wherein the marker is a dimer.

20. A method of performing microscopy on a sample material having at least one surface plasmon resonant marker attached thereto, the method comprising optically imaging the sample material and using a result to select a region of the sample material for imaging via electron microscopy, wherein the optically imaging the sample comprises:
    illuminating the sample material with stimulation light that will be absorbed by a marker and will be emitted as four-wave mixing light and
    discriminating the four-wave mixing light in light emanating from the sample zone,
    wherein illuminating the sample material comprises:
        emitting a train of pulses of laser light, and
        receiving said train of pulses in an arrangement of parallel optical paths, and
    wherein said arrangement of parallel optical paths is configured to:
        create first, second and third versions of a single pulse of said train of pulses, and
        convey said first, second and third versions of said single pulse to the sample zone such that the third version arrives at the sample zone after the second version and the second version arrives at the sample zone not earlier than the first version and not later than the first version by more than the dephasing time of the marker,
    wherein optically imaging the sample further comprises:
    bringing a fourth version of said single pulse into interaction with the light emanating from the sample zone, and
    wherein discriminating the four-wave mixing light comprises:
    detecting interference of the fourth version of said single pulse with four-wave mixing light triggered by the third version of said single pulse.

* * * * *